United States Patent [19]

Shin et al.

[11] 4,410,751

[45] Oct. 18, 1983

[54] PRODUCTION OF OLEFINS FROM A LOWER ALCOHOL OR DIMETHYL ETHER

[75] Inventors: Shigemitsu Shin, Yatabe; Kunio Suzuki, Sakura; Yoshimichi Kiyozumi, Yatabe; Kiyoshi Ogawa, Yokohama; Haruo Takaya, Abiko; Kenichiro Bando, Yatabe; Yasuo Takami, Tokyo; Yasuhiko Kohtoku, Tsuchiura; Hideo Watanabe, Tokyo; Kichinari Kawamura, Tsuchiura; Yuzi Shimazaki, Sakura, all of Japan

[73] Assignee: Director-General of Agency of Industrial Science & Technology, Tokyo, Japan

[21] Appl. No.: 357,461

[22] Filed: Mar. 12, 1982

[30] Foreign Application Priority Data

May 15, 1981 [JP] Japan .................................. 57-73939

[51] Int. Cl.³ ............................................. C07C 1/24
[52] U.S. Cl. ................................... 585/640; 502/242; 502/84
[58] Field of Search ..................... 585/640; 252/455 R

[56] References Cited

U.S. PATENT DOCUMENTS

| | | | |
|---|---|---|---|
| 2,378,236 | 6/1945 | Miller | 585/640 |
| 3,963,645 | 6/1976 | Gelbein | 252/455 R |
| 4,134,926 | 1/1979 | Tsad et al. | 585/640 |
| 4,176,090 | 11/1979 | Vaughan et al. | 252/455 R |
| 4,232,179 | 11/1980 | Barrocas et al. | 585/640 |

*Primary Examiner*—Delbert E. Gantz
*Assistant Examiner*—Anthony McFarlane
*Attorney, Agent, or Firm*—Stephen F. K. Yee

[57] ABSTRACT

A lower alcohol, especially methanol, or dimethyl ether is subjected to pyrolysis conditions in the presence of a specific catalyst to obtain lower olefins. The catalyst is comprised of a smectite, such as a montmorillonite clay, having superimposed aluminosilicate layers and zirconium oxide intercalated between the structural, aluminosilicate layers.

8 Claims, No Drawings

PRODUCTION OF OLEFINS FROM A LOWER ALCOHOL OR DIMETHYL ETHER

BACKGROUND OF THE INVENTION

This invention relates generally to a process for the production of olefins and, more particularly, to a process for the catalytic conversion of a lower alcohol or dimethyl ether into olefins.

For the conversion of methanol into olefins, a process is known in which a synthetic zeolite is used as catalyst. The zeolite catalyst, however, is not quite satisfactory. Firstly, it is very difficult to prepare zeolite having a desired catalytic performance. Secondly, the catalytic activity and selectivity of zeolite are not high enough to be used economically on a commercial scale.

BRIEF SUMMARY OF THE INVENTION

It is, therefore, an object of the present invention to provide an improved process which can convert dimethyl ether or a lower alcohol, especially methanol, into olefins, especially ethylene and propylene, with a high selectivity and a yield.

Another object of the present invention is to provide an economical process of the above-mentioned type using an easy to prepare catalyst.

Other objects, features and advantages of the present invention will become apparent from the detailed description of the invention to follow.

DETAILED DESCRIPTION OF THE INVENTION

The present invention provides an improved process for subjecting a lower alcohol or dimethyl ether to pyrolysis to obtain olefins. The improvement involves the step of contacting a gas stream containing a lower alcohol or dimethyl ether with a catalyst including a smectite composed of superimosed aluminosilicate layers, and zirconium oxide intercalated between the said layers. Thus, the catalyst used in the process of the present invention is comprised of a smectite as a host component and zirconium oxide as a guest component.

Smectites are swelling clay minerals in that they can take up water or organic liquids between their structural layers and show marked cation exchange properties. Illustrative of the smectites are montmorillonite, beidellite, nontronite, saponite, hectorite and sauconite. In addition to these smectites, clay minerals containing smectites as their principal constituents, such as bentonite clays, and terra abla clays may also be used as the starting material for the catalyst of this invention. Besides these naturally available clays, synthetic smectites such as obtained by the hydrothermal treatment of a natural clay mineral or a mixture of suitable raw materials, for example, a mixture of silica sol, sodium aluminate and magnesium hydroxide, may also be used.

The smectite mineral consists of superimposed aluminosilicate layers, each of which is composed of a sheet of $AlO_4(OH)_2$ octahedra sandwiched between two sheets of $SiO_4$ tetrahedra. Details of smectites are shown, for example, in W. A. Deer, R. A. Howie and J. Zussman, "Rock-Forming Minerals", vol. 3 (Sheet Silicate), p. 226. LongMans, Green and Co., Ltd., London, United Kingdom (1963).

Intercalated between the structural, aluminosilicate layers of the smectite is zirconium oxide which forms pillars between sheets of $SiO_4$ tetrahedra of adjacent aluminosilicate layers. Thus, within the inter-layer space of the smectite, a multiplicity of pores defined by the intercalated, zirconium oxide pillars are formed. The amount of zirconium oxide is preferably between about 5 and 50%, more preferably between about 10 and 30%, based on the weight of the catalyst.

The catalyst having the following physical properties are preferably used in the process of this invention. The average pore diameter, which can have an influence upon the selectivity, is in the range of about 3 and 10 Å, preferably about 4 and 9 Å. The surface area can have an influence upon the catalytic activity and is in the range of about 10 and 500 $m^2/g$, preferably between about 150 and 400 $m^2/g$. The pore volume is in the range of between about 0.1 and 0.4 cc/g, preferably between about 0.25 and 0.35 cc/g. In this connection, it is preferred that pores with diameters of between 4 and 6 Å occupy about 40-100% of the total pore volume. The catalyst may be regarded as crystalline material from the standpoint of X-ray crystallography and exhibits a basal reflection at about 14.6 to 18.8 Å.

The intercalation catalyst may be prepared in the following manner. A smectite or a substance containing a smectite as its principal ingredient is dispersed in a solution containing zirconium compound capable of providing hydroxy-zirconium cation so that the hydroxy-zirconium cation may be ion-exchanged for cations originally contained in the smectite. Examples of such zirconium compounds include zirconium hydroxide, zirconyl chloride, zirconyl nitrate, zirconyl phosphate, zirconyl acetate and zirconium acetylacetonate. The concentration of the zirconium compound in the solution is generally 0.025 to 1 mol/l.

The cation exchange reaction may be expressed:

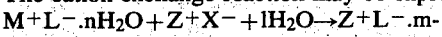

wherein $M^+$ stands for an ion-exchangeable cation contained in a smectite, such as alkali metal ion and alkaline earth metal ion; $L^-$ stands for anionic layer of the smectite; $nH_2O$ stands for interlayer water; $Z^+$ stands for zirconium ion $Zr^{4+}$ and hydroxy-zirconium cation originated from a zirconium compound; $X^-$ stands for organic or inorganic anion constituting the zirconium compound; $lH_2O$ stands for the water in the aqueous solution of the zirconium compound; and l, m and n each stand for a positive number.

The cation-exchange reaction may be performed at a temperature of up to 100° C. with stirring or under reflux conditions. The reaction may also be carried out by way of a hydrothermal method in which the dispersion is reacted at a temperature over 100° C. under a pressure.

The resulting smectite containing hydroxy-zirconium cation is then washed, dried and thermally treated at a temperature of 100°–700° C., preferably 300°–600° C., so that the hydroxy-zirconium cation is converted into zirconium oxide by dehydroxylation with the simultaneous formation of pores defined by the zirconium oxide pillars between the inter-layer space. The heat treatment may be performed under vacuum or in the atmosphere of air, oxygen or inert gas such as nitrogen, helium or argon, to facilitate the dehydration.

In the process of this invention, a gas stream containing a raw material of the formula:

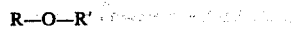

wherein R is a lower alkyl group, preferably having 1-4 carbon atoms and R' is hydrogen or a methyl group with the proviso that when R' is methyl, R is methyl, is contacted with the above intercalation catalyst at a temperature of 200°-500° C., preferably 300°-400° C., and a partial pressure of the raw material of 0.1-50 Kg/cm², preferably 0.5-20 Kg/cm², whereby to obtain olefins mainly having 2-4 carbon atoms. The hourly liquid space velocity is generally in the range of 0.1-20 $Hr^{-1}$.

The following example will further illustrate the present invention.

EXAMPLE 20 g of Na-montmorillonite (produced in Aterazawa Mine, Yamagata-ken, Japan) were mixed with one liter of 1 M $ZrOCl_2$ aqueous solution and the mixture was reacted at 80° C. for 1.5 hours with stirring, whereby the cation-exchangeable cations of the montmorillonite were exchanged with hydroxy-zirconium cation. After completion of the cation-exchange reaction, the reaction mixture was left stand quiescently at room temperature. After the removal of the supernatant liquid by decantation, the precipitate was washed with ion-exchanged water until no chloride ion was detected. The washed precipitate was subsequently dried in air at 100° C. for 3 hours by means of an electric oven to obtain a catalyst precursor. The precursor material was then calcined at 500° C. for 20 hours in air to obtain a catalyst (hereinafter referred to as Catalyst I). The X-ray diffraction patterns of the montmorillonite clay, the catalyst precursor and Catalyst I are shown below by way of a table. The X-ray diffraction measurement was carried out in the following conditions.

X-ray tube: Operating with 40 KV, 30 mA (Ni filter was used)
Goniometer scan speed: 2°/min
Chart speed: 2 cm/min

TABLE 1

| X-ray Diffraction Pattern of Montmorillonite Clay | | |
|---|---|---|
| Latice Spacing, d (Å) | Index of Plane (hkl) | Relative Intensity $I/I_O$* |
| 12.3 | 001 | vs |
| 6.2 | 002 | w |
| 4.3 | 003 | w |
| 3.1 | 004 | s |
| 2.6 | 005 | w |
| 2.1 | 006 | w |

*X-ray reflection intensity
vs: very strong
s: strong
w: weak

TABLE 2

| X-ray Diffraction Pattern of Catalyst Precursor | |
|---|---|
| Latice Spacing, d (Å) | Relative Intensity $I/I_O$ |
| 16.1 | s |
| 11.3 | w |
| 5.8 | w |
| 2.6 | w |

TABLE 3

| X-ray Diffraction Pattern of Catalyst I | | |
|---|---|---|
| Latice Spacing, d (Å) | Index of Plane (hkl) | Relative Intensity $I/I_O$ |
| 7.3 | 002 | s |

As shown in Table 1, the montmorillonite clay, used as a starting clay material of Catalyst I, exhibits the basal reflection $d_{001}$ at 12.3 Å, which indicates that the clay is of a typical alkali-montmorillonite having ideal chemical formula $Na_{1/3}[(Mg_{1/3}Al_{5/3})Si_4O_{10}(OH)_2].2-H_2O$. On the other hand, the first diffraction peak in the case of the catalyst precursor appears at 16.1 Å (Table 2), indicating that hydroxy-zirconium cation has been incorporated in the inter-layer space by cation-exchange. The first diffraction peak shifts to 7.3 Å (Table 3) in the case of Catalyst I. Since deionized and dehydrated montmorillonite with its inter-layer space being fully collapsed, has a basal spacing $d_{001}$ at 9.6 Å, the diffraction peak at 7.3 Å is regarded as being attributed to the secondary reflection $d_{002}$. That is, Catalyst I is considered to have the basal reflection $d_{001}$ at 14.6 Å. Thus, it is considered that the inter-layer spacing (i.e. pore diameter) of Catalyst I is 5 Å (14.6 Å - 9.6 Å).

In order to confirm that Catalyst I in fact has inter-layer spacing of 5 Å, absorption characteristics of Catalyst I were examined using hexane isomers in the following manner. 100 mg of Catalyst I were packed in a reaction column having an inner diameter of 3 mm and heated at 500° C. for 1 hour in the atmosphere of helium and, thereafter, cooled to room temperature by a helium gas flow. After the pretreatment, a mixed gas containing equal proportion of 2,2-dimethylbutane (effective molecular size: 7.0 Å), 3-methylpentane (5.6 Å) and n-hexane (3.1 Å) was intermittently fed by a pulse method in an amount of 2 μl per one pulse, together with a helium gas (flow rate: 22 ml/min) serving as a carrier gas. The effluent gas in each pulse was introduced into a gas chromatograph for the analysis of its composition. As a result, 2,2-dimethylbutane was found not be adsorbed by Catalyst I. 3-Methylpentane and n-hexane were found to be adsorbed by Catalyst I but were desorbed therefrom in the second and third pulses, respectively. Accordingly, it is concluded that the effective pore diameter of Catalyst I is about 5 Å.

The specific surface area of Catalyst I measured by nitrogen adsorpotion method was 133.5 m²/g. For the purpose of comparison, the montmorillonite clay without Zr being exchanged was subjected to the same drying and calcination conditions as those described above to obtain a calcined product (hereinafter referred to as Catalyst II).

Catalytic decomposition of methanol was conducted using Catalyst I and Catalyst II at different temperatures. Thus, a stainless steel tube having 10 mm inner diameter was packed with 2 ml of catalyst sample, through which an argon gas was streamed at 500° C. for 3 hours at a flow rate of 40 ml/min. Thereafter, methanol vapor was fed into the tube at a flow rate of 2 ml/hour (as liquid methanol) together with argon gas (flow rate: 2 ml/min) serving as a carrier gas. The decomposition of methanol was carried out at 300°, 350° and 400° C. with a hourly liquid space velocity of 1 $H_r^{-1}$. The effluent gas was introduced into a gas chromatograph for the analysis of the composition of the product having 1 to 5 carbon atoms. The results are summarized in Table 4.

TABLE 4

| Product | Yield (g) | | | | | |
|---|---|---|---|---|---|---|
| | 300° C. | | 350° C. | | 400° C. | |
| | Cat. I | Cat. II | Cat. I | Cat. II | Cat. I | Cat. II |
| $CO_2$ | trace | trace | 0.04 | 0.01 | 0.30 | 0.08 |
| CO | 0.12 | trace | 0.21 | trace | 0.87 | 0 |
| Dimethyl Ether | 8.86 | 0.09 | 9.30 | 0.29 | 9.37 | 1.13 |
| Methane | 0.01 | trace | 0.07 | 0.05 | 0.75 | 0.35 |
| Ethylene | 0.17 | trace | 0.47 | 0 | 0.34 | 0.01 |
| Ethane | 0.02 | trace | 0.02 | 0 | 0.14 | 0.01 |
| Propene | 0.22 | trace | 0.57 | 0.01 | 0.43 | trace |
| Propane | 0 | 0.01 | 0 | trace | 0.08 | trace |
| iso-Butane | 0.22 | 0 | 0.39 | 0 | 0.19 | 0 |
| n-Butane | 0.17 | 0 | 0.31 | 0 | 0.19 | 0 |
| trans-Butene | 0.06 | 0 | 0.11 | 0 | 0.07 | 0 |
| cis-Butene | 0.03 | 0 | 0.07 | 0 | 0.04 | 0 |
| iso-Pentane | 0.11 | 0 | 0.23 | 0 | 0.15 | 0 |
| n-Pentane | 0.02 | 0 | 0.02 | 0 | 0.04 | 0 |

Remarks:
"Trace" means an amount less than 0.005 g.
"Yield" means single pass yields of $C_1$—$C_5$ compounds (g) per 100 g methanol charged.

On the basis of the results in Table 4, selectivity to respective $C_1$ to $C_5$ hydrocarbons with catalyst I was calculated and the results are as shown in Table 5.

TABLE 5

| Product | Selectivity (wt %) | | |
|---|---|---|---|
| | 300° C. | 350° C. | 400° C. |
| Methane | 0.82 | 3.10 | 30.92 |
| Ethylene | 16.77 | 20.76 | 14.25 |
| Ethane | 0.20 | 1.02 | 5.94 |
| Propene | 22.26 | 25.44 | 17.70 |
| Propane | 0 | 0 | 3.51 |
| iso-Butane | 22.17 | 17.28 | 7.72 |
| n-Butane | 16.35 | 13.64 | 7.95 |
| trans-Butene | 5.46 | 4.74 | 2.72 |
| cis-Butene | 3.30 | 3.06 | 1.54 |
| iso-Pentane | 11.04 | 10.06 | 6.13 |
| n-Pentane | 1.62 | 0.91 | 1.60 |

As will be appreciated from the results in Table 4, montmorillonite catalyst (Catalyst II) fails to yield hydrocarbons other than methane and is not suited for use as a catalyst for the production of lower olefins. The Zr-intercalation catalyst (Catalyst I) of this invention, on the other hand, can produce a fair amount of lower hydrocarbons. Moreover, as is seen from Table 5, the selectivity to lower olefins, especially ethylene and propylene, is very high.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

We claim:

1. A process for subjecting methanol or dimethyl ether to pyrolysis to obtain olefins, comprising contacting a gas stream containing methanol or dimethyl ether with a catalyst which comprises a smectite composed of superimposed aluminosilicate layers, and zirconium oxide intercalated between said layers.

2. A process as claimed in claim 1, wherein said smectite is a clay mineral selected from the group consisting of montmorillonite, beidellite, nontronite, saponite, hectorite and sauconite.

3. A process as claimed in claim 1, wherein said smectite is that contained in bentonite or terra abla.

4. A process as claimed in claim 1, wherein said smectite is a synthetic smectite.

5. A process as claimed in claim 1, wherein said catalyst has a basal spacing at between 14.6 and 18.8 Å.

6. A process as claimed in claim 1, wherein said catalyst has a specific surface area of between about 10 and 500 m²/g, a pore volume of between about 0.1 and 0.4 cc/g and an average pore diameter of between about 3 and 10 Å.

7. A process as claimed in claim 1, wherein said catalyst is obtained by a method which comprises the steps of:

mixing a smectite with an aqueous solution containing a zirconium compound capable of providing hydroxy-zirconium cation to exchange the cations of the smectite with the hydroxy-zirconium cation; and drying and calcining the hydroxy-zirconium-carrying smectite.

8. A process as claimed in claim 1, wherein said contact is carried out at a temperature of between 200° and 500° C. and an hourly liquid space velocity of between 0.1 and 20 $Hr^{-1}$.

* * * * *